United States Patent [19]

Lovison

[11] 4,022,212
[45] May 10, 1977

[54] HYGIENIC GARMENT ASSEMBLY

[76] Inventor: Paula J. Lovison, 916 N. First St., Alhambra, Calif. 91801

[22] Filed: Aug. 7, 1975

[21] Appl. No.: 602,652

[52] U.S. Cl. .............................. 128/288; 128/290 R
[51] Int. Cl.² ..................... A61F 13/16; A41B 13/02
[58] Field of Search .......... 128/286, 284, 287, 288, 128/289, 290 R, DIG. 15

[56] References Cited

UNITED STATES PATENTS

| 791,354 | 5/1905 | Merkley | 128/290 R |
| 1,830,528 | 11/1931 | Cohon | 128/288 X |
| 2,175,786 | 10/1939 | Smarr | 128/288 |
| 3,057,354 | 10/1962 | Roberts et al. | 128/289 |
| 3,397,697 | 8/1968 | Rickard | 128/288 |
| 3,460,535 | 8/1969 | Behna | 128/288 |
| 3,804,093 | 4/1974 | Fell | 128/286 |

FOREIGN PATENTS OR APPLICATIONS

| 436,766 | 6/1948 | Italy | 128/288 |

Primary Examiner—Aldrich F. Medbery

[57] ABSTRACT

A hygienic garment assembly including a panty-type garment which is devoid of a crotch portion with the front and rear panels being cut off horizontally and hemmed, and a sanitary napkin which constitutes the crotch portion of the garment assembly, the ends of the napkin being fastened by detachable means to the hems of the front and rear panels, respectively.

2 Claims, 4 Drawing Figures

HYGIENIC GARMENT ASSEMBLY

BACKGROUND OF THE INVENTION

The wearing of sanitary napkins or the like is a problem with which women are confronted quite regularly. Despite the large amount of known technology in this field, improvement is still possible. For the user the main considerations are convenience, economy, and effectiveness.

Convenience requires ease in fitting the sanitary napkin and/or its holder, as well as ease in putting it on and taking it off. Convenience also requires comfort while wearing the napkin and its holder. Economy involves the initial cost of sanitary napkins and related garments, as well as useful life. Effectiveness involves the efficiency of the sanitary napkin and its accessories in controlling and disposing of bodily excretions.

Economy of manufacture is also a requirement. An important aspect of manufacturing cost is whether one size of sanitary napkin and/or its accessories can be made to fit women of widely varying body sizes and shapes.

The object and purpose of the invention is to provide a sanitary napkin and supporting garment therefor, which are convenient and effective in usage, and yet economical to make. More specifically, the object and purpose of the invention is to provide a new type of sanitary napkin with its supporting garment, a single size of which will fit a large number of women of varying body sizes and shapes.

PRIOR ART

Among the relevant United States patents are the following:

M. S. Merkley U.S. Pat. No. 791,354
M. E. Lane U.S. Pat. No. 2,030,306
J. Cline U.S. Pat. No. 2,977,957

SUMMARY OF THE INVENTION

According to the invention a panty-type garment is made without a crotch portion, the depending front and rear panels of the garment being cut off along horizontal lines and hemmed. The sanitary napkin is used to provide the crotch portion of the complete garment assembly. The ends of the sanitary napkin are fastened, by detachable means, to the hemmed lower edges of the front and rear panels previously referred to.

The panty-type garment in accordance with the present invention has no separate utility. It is used only in conjunction with a sanitary napkin. If a sanitary napkin is not going to be worn, then the panty-type garment is not used.

According to the invention the sanitary napkin is not made of rectangular configuration, but rather, its longitudinal side edges are concavely curved inwardly. It is significantly wider at its ends than in its longitudinal center. This configuration of the napkin permits effective support of it from the panty-type garment and more particularly, effective support from the corners of the napkin.

Further in accordance with the invention, it is greatly preferred to make the panty-type garment of an elastic material throughout while the sanitary napkin is so constructed as to be essentially inelastic. The reason for this type of construction is that women of varying body sizes and shapes nevertheless tend to be of very much the same size and shape in the crotch portion. A single size of the panty-type garment, being elastic, will accommodate almost any size of wearer. Stretching of the sanitary napkin is not required since, as previously pointed out, a single size will fit essentially all wearers.

Also in accordance with the invention, the preferred type of fastening means includes permanent hooks which are secured to the hems at the lowermost edges of the panty-type garment, and flexible loops adjacent the ends of the sanitary napkin.

In accordance with the invention the panty-type garment is, preferably though not necessarily, continuously reusable over a long period of time. The sanitary napkin is disposable and must be replaced from time to time.

DRAWING SUMMARY

PREFERRED EMBODIMENT

Figures 1, 2, 3, 4:
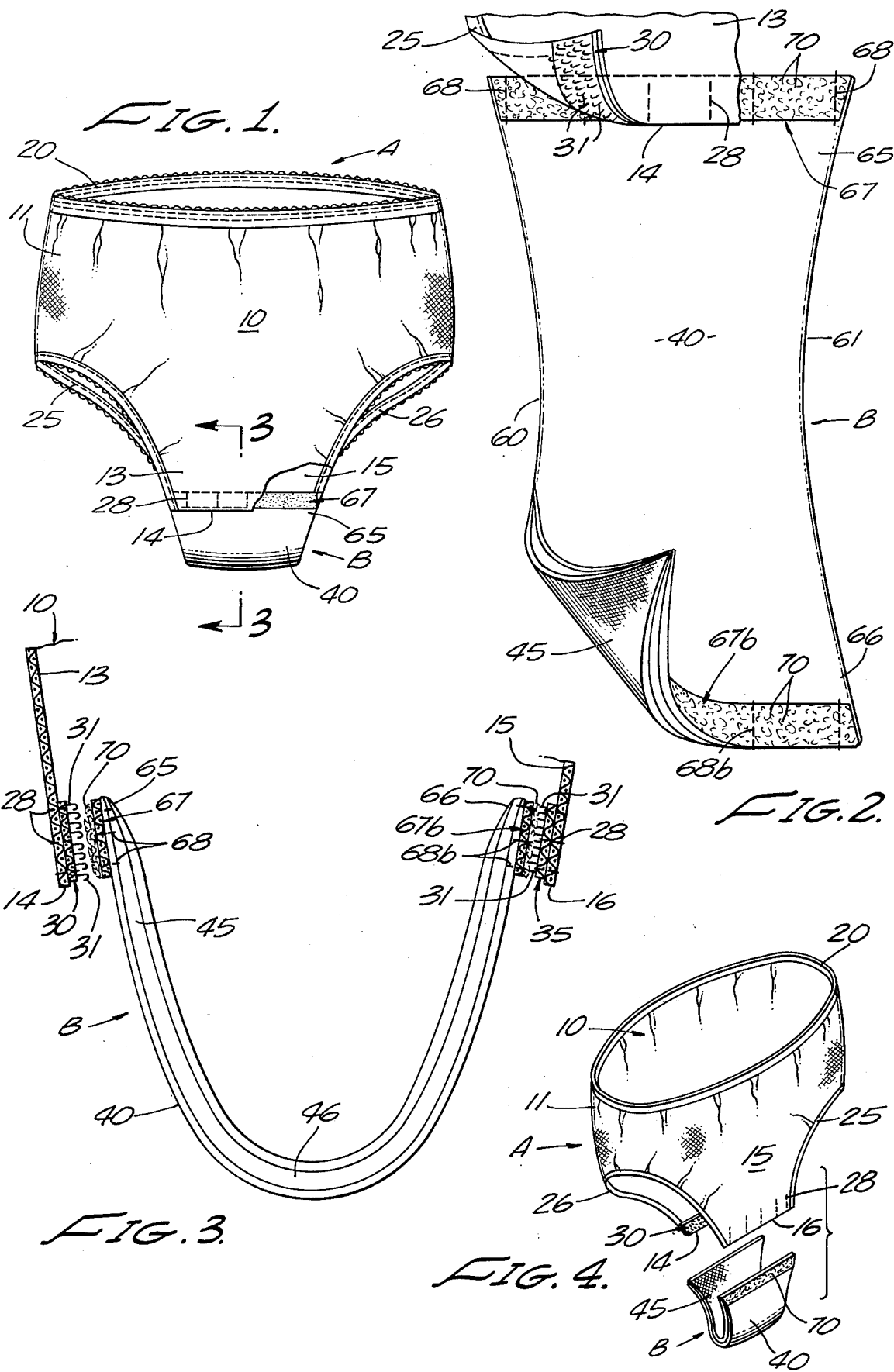
FIG. 1 is a front elevation view of a garment assembly in accordance with the invention.
FIG. 2 is a view of the under side of the napkin, showing one end attached and the other end free.
FIG. 3 is a cross-sectional elevational view taken on the line 3—3 of FIG. 1.
FIG. 4 is a perspective view of the rear side of the invention when disassembled.

Reference is now made to the drawing, FIGS. 1 through 4, inclusive, illustrating the presently preferred form of the invention. In general a hygienic garment assembly in accordance with the invention includes a panty-type garment A to which a sanitary napkin B is removably attached.

More particularly, the garment A is formed from an elastic sheet member 10 having a trunk portion 11. A front panel 13 depends downwardly from the front side of the trunk portion while a rear panel 15 depends downwardly from its rear side. The garment A is devoid of a crotch portion, and the lower edge 14 of front panel 13 and lower edge 16 of rear panel 15 are accordingly cut along horizontal lines. A horizontally extending fastening strip 30 is secured to the inner surface of the lower edge 14 thereof. Similarly, a fastening strip 35 which extends horizontally covers the inner surface of the lower edge 16 of rear panel 15. Each fastening strip is secured to its associated panel preferably by means of stitches 28 (FIG. 3).

Garment A also includes a waistband 20, secured to the upper edge of sheet member 10 around its entire periphery. Waistband 20 is preferably made of an elastic material. Garment A also includes legbands 25, 26. The right legband 25 extends upwardly along the right side of the front panel 13, hence across the lower edge of the trunk portion 11, and hence down the right side edge of the rear panel 15. The left legband 26 is secured in similar fashion to the other side of the garment. The legbands 25, 26 are preferably made of elastic material.

In the particular construction of garment A as shown, the elastic legbands 25, 26 are sewed to the elastic sheet member 10 before the fastening strips 30, 35 are placed on the garment. Each fastening strip, therefore, is attached to one truncated end of each of the legbands.

Each of the fastening strips 30, 35 has attached thereto a plurality of protruding hooks 31 which are stiff hook shaped needle-like locking fingers arranged in opposing rows. The fastening strip with hooks incorporated therein is a commercially available product well known in the art.

Sanitary napkin B includes a backing sheet 40 which is moisture resistant. An absorbent pad 45 is carried upon the upper surface of the backing sheet 40. Both the backing sheet and the absorbent pad are of the same general configuration, generally rectangular but with their longitudinal side edges 60, 61 being concavely curved inwardly (see FIG. 2). The result is that the end portions of the napkin are significantly wider than its longitudinal center portion.

In the drawing the two ends of the napkin, though identical, are identified for convenience by numerals 65, 66, respectively. End portion 65 has a fastening strip 67 secured by means of stitches 68 to the outer surface of backing sheet 40. Strip 67 has a relatively high pile nap surface defined by a myriad of looped soft fibers 70. End portion 66 has fastening strip 67b secured by stitches 68b with similar looped fibers 70.

It will be understood that fastening strip 67 with its looped fibers 70 is also well-known in the art and is commercially available, and adapted to cooperate with the hooks 31 of fastening strip 30.

In the assembled form of the invention, the pad end portions 65, 66 are curved upwardly as shown in FIG. 3 and are placed inside the fastening strips 30, 35, respectively. The flexible loops 70 of the pad are then hooked over the hook ends of the hook members 31 of garment A.

When the napkin is to be disposed of, the hooks are detached from the hooks of the garment, and a new napkin is attached in place of the original one.

ALTERNATE FORMS

While the absorbent pad 45 is preferably thickened at its lateral center 46 as shown (FIG. 3) it may nevertheless be made of uniform thickness throughout its width if that is desired.

While the hook and loop fasteners are preferred, the invention is not to be thus limited, and any satisfactory type of detachable fasteners may be used as desired.

The invention has been described in considerable detail in order to comply with the patent laws by providing a full public disclosure of at least one of its forms. However, such detailed description is not intended in any way to limit the broad features or principles of the invention, or the scope of patent monopoly to be granted.

What is claimed is:

1. A hygienic garment assembly comprising:
   a panty-type garment including an elastic sheet member forming a trunk portion and front and rear panels depending downwardly from said trunk portion, an elastic waistband secured to the upper edge of said trunk portion, and a pair of elastic legbands secured to corresponding lower side edges of said trunk portion and having front and rear ends secured to the associated side edges of said front and rear panels, said garment being devoid of a crotch portion and said front and rear panels being horizontally truncated and having horizontally extending fastening strips extending across their lower edges, said fastening strips being also secured to respective front and rear ends of said legbands;
   a sanitary napkin having a generally elongated rectangular configuration but with the longitudinal side edges thereof being concavely inwardly curved, said napkin including a moisture-resistant sheet member made of an inelastic material forming the bottom part thereof, an absorbent material carried above said sheet member, and horizontally extending fastening strips carried across the respective ends of said napkin; and
   means detachably fastening the fastening strips of said napkin to the respective fastening strips of said front and rear panels, said naplin thereby providing the crotch portion of the garment assembly;
   the longitudinal side edges of said napkin being inelastic but the legbands contiguous therewith being elastic, whereby the garment assembly will fit women of varying body sizes and shapes while still providing body-fitting support for said napkin.

2. The garment assembly of claim 1 wherein said fastening means includes a plurality of hooks carried by the exterior surface of each of said fastening strips of said panty type garment, and a plurality of flexible loops attached to the outer surface of said fastening strips of said napkin member at a location spaced inwardly from the end thereof; said loops being engaged with said hooks, and the associated portion of said napkin being disposed in contact with the inner surface of the respective one of said fastening strips.

* * * * *